(12) United States Patent
Ikebukuro et al.

(10) Patent No.: US 8,310,676 B2
(45) Date of Patent: Nov. 13, 2012

(54) METHOD AND APPARATUS FOR DETECTING SMALL BIOMOLECULES

(75) Inventors: Kazunori Ikebukuro, Fuchu (JP); Ryo Katayama, Kobe (JP); Eiji Takahashi, Kobe (JP)

(73) Assignee: Kobe Steel, Ltd., Kobe-shi (JP)

( * ) Notice: Subject to any disclaimer, the term of this patent is extended or adjusted under 35 U.S.C. 154(b) by 142 days.

(21) Appl. No.: 12/667,585

(22) PCT Filed: Jul. 3, 2008

(86) PCT No.: PCT/JP2008/062055
§ 371 (c)(1),
(2), (4) Date: Apr. 22, 2010

(87) PCT Pub. No.: WO2009/005117
PCT Pub. Date: Jan. 8, 2009

(65) Prior Publication Data
US 2011/0007317 A1    Jan. 13, 2011

(30) Foreign Application Priority Data
Jul. 4, 2007    (JP) .................. 2007-176313

(51) Int. Cl.
*G01N 21/00*    (2006.01)
(52) U.S. Cl. ......... 356/432; 356/445; 356/51; 435/6.12; 435/214; 435/7.1
(58) Field of Classification Search .................. 356/432, 356/51, 445; 435/6, 6.11, 6.12, 39, 7.1, 6.18, 435/214
See application file for complete search history.

(56) References Cited

U.S. PATENT DOCUMENTS

| 4,243,327 A | 1/1981 | Frosch et al. |
| 5,439,830 A | 8/1995 | Sakashita et al. |
| 6,884,582 B1 | 4/2005 | Chaton et al. |

(Continued)

FOREIGN PATENT DOCUMENTS

EP    0 594 412 A1    4/1994

(Continued)

OTHER PUBLICATIONS

Kazunori Ikebukuro, et al., "Construction of the novel protein detection system using IER method", Abstracts of the Annual Meeting of the Society for Biotechnology, Aug. 25, 2004, p. 241 (with English Translation and an additional page).

(Continued)

*Primary Examiner* — Gregory J Toatley
*Assistant Examiner* — Iyabo S Alli
(74) *Attorney, Agent, or Firm* — Oblon, Spivak, McClelland, Maier & Neustadt, L.L.P.

(57) ABSTRACT

An object of the present invention is to detect a small biomolecule in a sample using simple and inexpensive equipment. To achieve this, the small biomolecule in a sample S is detected optically. Specifically, the sample S containing an aptamer capable of interacting with the small biomolecule is irradiated with an excitation light Le and irradiated with a measurement light L2 for measuring the photothermal effect produced in the sample S by the irradiation with the excitation light Le. The photothermal effect induced in the sample S by the excitation light Le is measured from the phase change in the measurement light L2, and the presence or absence of the interaction between the biomolecule and the aptamer is assessed based on the temporal variation in the measurement signal.

8 Claims, 7 Drawing Sheets

U.S. PATENT DOCUMENTS

| | | | |
|---|---|---|---|
| 2006/0014172 | A1 | 1/2006 | Muller et al. |
| 2010/0159451 | A1* | 6/2010 | Ikebukuro et al. ............ 435/6 |

FOREIGN PATENT DOCUMENTS

| | | |
|---|---|---|
| EP | 2 021 066 A1 | 4/2009 |
| FR | 2 799 281 A1 | 4/2001 |
| JP | 2001-165939 | 6/2001 |
| JP | 2004-156925 | 6/2004 |
| JP | 2004-301520 | 10/2004 |
| JP | 2005-283566 | 10/2005 |
| JP | 2006-84431 | 3/2006 |
| JP | 2006-226880 | 8/2006 |
| WO | WO 02/090912 A1 | 11/2002 |
| WO | WO 2005/113817 A2 | 12/2005 |
| WO | WO 2005/113817 A3 | 12/2005 |
| WO | WO 2006/033348 A1 | 3/2006 |
| WO | WO 2007/145298 A1 | 12/2007 |

OTHER PUBLICATIONS

Naokazu Sakoda, et al., "Detection of Trace Amount of Biomolecules by Laser Interferometric Photothermal Measurement (II)", Japan Society of Applied Physics and Related Societies, vol. 52 & vol. 3, p. 1135 (with English Translation and an additional page).

Eiji Takahashi, et al., High-sensitivity light absorption spectrometry by laser interferometric photothermal measurement (2), Abstracts of the Symposium of the Japan Society for Analytical Chemistry, vol. 67, Apr. 29, 2006, p. 87 (with English Translation and an additional page).

Extended European Search Report issued Sep. 2, 2011, in Patent Application No. 08777807.2.

Hajime Sakashita, et al., "Homogeneous Immunoassay Using Photothermal Beam Deflection Spectroscopy", Analytical Chemistry, vol. 67, No. 7, XP 501334, Apr. 1, 1995, pp. 1278-1282.

Jianhua Zhao, et al., "Thermophysical property measurements using time-resolved photothermal deflection spectrometry with step optical excitation", Applied Physics Letters, vol. 84, No. 26, XP 12073105, Jun. 2004, pp. 5332-5334.

Tamao Odake, et al., "High-Speed Separation Using Miniaturized Slab Gel and High Spatial Resolution Detection by Thermal Lens Microscope", Proceedings of the SPIE, The International Society for Optical Engineering, SPIE, vol. 3565, XP 925278, Jan. 1999, pp. 126-133.

K. Adelhelm, et al., "Development of a sensitive detection system based on the photothermal effect for biomolecular interaction studies", Proceedings of the SPIE, The International Society for Optical Engineering, SPIE, vol. 2629, XP 925207, Jan. 1996, pp. 325-333.

* cited by examiner

TIME LAG CORRECTION

METHOD AND APPARATUS FOR DETECTING SMALL BIOMOLECULES

TECHNICAL FIELD

The present invention relates to a technology for detecting small biomolecules such as sugars (sugar chains), nucleosides, hormones and vitamins, which have relatively small molecular weights, by utilizing the interactions of small biomolecules.

BACKGROUND ART

Biomolecules include small biomolecules, which have relatively small molecular weights, such as sugars (sugar chains), nucleosides, hormones, vitamins, and so forth. These small biomolecules, which frequently lack a characteristic light absorption spectrum, are hard to be detected and identified by only so-called spectroscopic methods.

As means for detecting the small biomolecule, can be contemplated an method utilizing an interaction between such a small biomolecule and another substance. For example, Patent Document 1 discloses a method of detecting an interaction between a protein and a small molecule, which method includes analyzing a structural change in a protein produced by the incorporation of a small molecule at the protein's active site, for example, NMR, and determining the structure of the small molecule with a mass spectrometer. Patent Document 2 discloses a method that uses a surface-localized plasmon resonance (SPR) sensor, which method includes solid phase-bonding a sample on a thin metal film formed on a substrate and detecting the degree of absorption of specific incident laser light on the sample, by use of the SPR.

However, the method disclosed in Patent Document 1 requires a substantial number of large and expensive instruments, i.e., a liquid chromatograph, NMR, and mass spectrograph. On the other side, the method disclosed in Patent Document 2 requires the immobilization of an auxiliary molecule on the metal surface and the detection at high reproducibilities requires an extremely high degree of technique.

A fluorescent method, though being known as simple and highly sensitive methods for detecting the interaction between nucleic acid and protein, are unsuitable for the detection of the small biomolecules referenced above. The fluorescent method includes labeling both of the interacting substances (for example, nucleic acid and protein) with different fluorescent dyes which interact with each other to enable the fluorescence to be changed, and measuring whether the change actually occurs; however, it is quite difficult to label small molecules with these fluorescent dyes. Even if it can be done, the fluorescent dye may exert such an influence on an active site as to interfere with a normal reaction.

[Patent Document 1] Japanese Patent Application Laid-open No. 2006-226880
[Patent Document 2] Japanese Patent Application Laid-open No. 2005-283566

DISCLOSURE OF THE INVENTION

Considering the circumstances outlined above, an object of the present invention is to provide a technology that enables a small biomolecule in a sample to be detected with high sensitivity by use of simple and inexpensive equipment.

In order to achieve this object, the present inventors took note of the photothermal effect—i.e., the effect that a sample absorbs a specific excitation light directed onto the sample to generating heat—that occurs when the interaction of a small biomolecule is caused in a sample, and thereby have discovered a significant correlation between the photothermal effect and the presence or absence of the interaction between a small biomolecule and its aptamer in the sample. Specifically, it has been discovered that, although the photothermal effect generally declines with elapsed time, the photothermal effect caused in a sample having an interaction between a small biomolecule and its aptamer therein is hardly timewise declined at least immediately after the rise in the photothermal effect. This is due presumably to stabilization of the aptamer because of the interaction between aptamer and its target, that is, the small biomolecule.

The present invention, achieved by focusing on the above point, provides a method of detecting a small biomolecule in a sample, comprising:

a step of irradiating a sample containing an aptamer that can interact with the small biomolecule with an excitation light;

a step of measuring a photothermal effect that is produced in the sample by the irradiation with the excitation light; and a step of detecting the presence or absence of the small biomolecule by assessing, on the basis of the temporal variation in the photothermal effect, whether or not interaction between the small biomolecule and aptamer has occurred in the sample.

The present invention also provides an apparatus for detecting a small biomolecule in a sample, comprising:

a sample holding section for holding a sample that contains an aptamer that can interact with the small biomolecule;

an excitation light irradiation system that irradiates a sample held in the sample holding section with an excitation light; and a measurement apparatus that produces a measurement signal of a photothermal effect caused in the sample by the irradiation with the excitation light, the measurement apparatus including a signal processing apparatus that generates data on a temporal variation in the measurement signal and assesses, based on the generated data, whether or not the interaction is present to detect the presence or absence of the small biomolecule.

According to the method and the apparatus, measuring the photothermal effect caused in the sample irradiated with excitation light and monitoring the temporal variation in the photothermal effect make it possible to assess the presence or absence of the interaction between the small biomolecule and its aptamer, thereby enabling the presence or absence of the small biomolecule itself to be accurately assessed. As a consequence, without attaching a label to the small biomolecule in the sample and immobilizing the sample on a metal thin film, the presence/absence of the interaction and further the presence/absence of the small biomolecule can be easily detected at high sensitivities. In addition, the signal processing apparatus in the detection apparatus generates data useful for assessing the presence/absence of this interaction to automatically assess the presence/absence of the interaction based on this data, thereby detecting whether or not the small biomolecule is present.

The small biomolecule referenced herein is a biomolecule that have a relatively small molecular weight from approximately several hundred to several thousand and is an organic molecule as typified by sugar, nucleoside, hormone, and vitamin.

BEST MODE FOR CARRYING OUT THE INVENTION

A first embodiment of the present invention will be described with reference to FIGS. 1 to 5.

Figure 1:
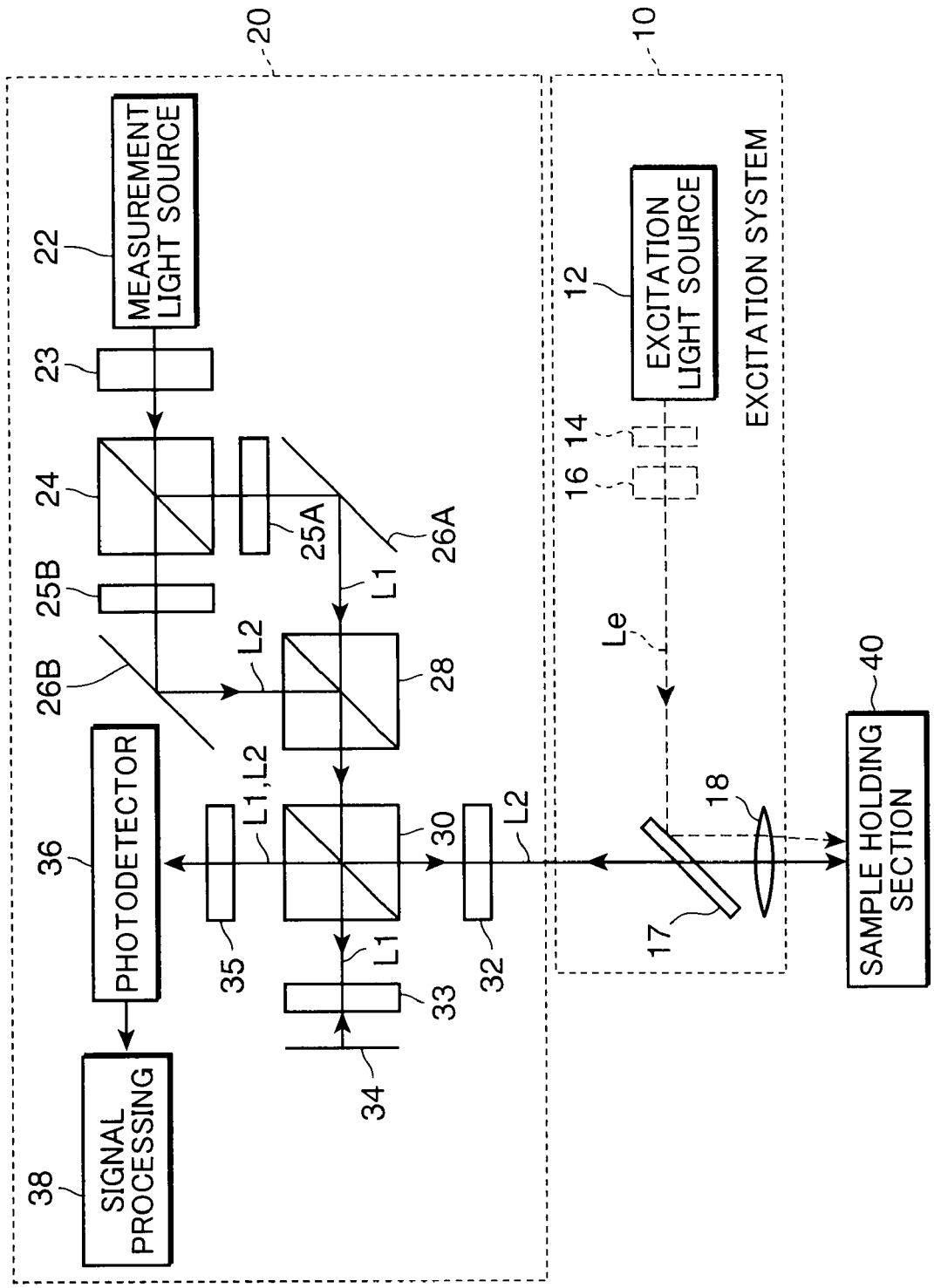
FIG. 1 is a diagram that shows the whole structure, according to a first embodiment of the present invention, of the apparatus for detecting interaction between a small biomolecule and its aptamer.

FIG. 1 shows a whole structure of a detection device according to this embodiment. The shown detection device comprises an excitation light irradiation system (referred to hereafter simply as "excitation system") 10, a measurement system (measurement apparatus) 20, and a sample holding section 40, which holds the sample described below.

The excitation system 10 operates to irradiate the sample held in a specified position in the sample holding section 40 with a excitation light, comprising an excitation light source 12, a spectroscopic mechanism 14, a modulation mechanism 16, a dichroic mirror 17, and a condensing lens 18.

The excitation light source 12 is suitably, for example, a xenon lamp that outputs white light or a mercury lamp that outputs ultraviolet light. The light emitted from the excitation light source 12 is dispersed by the spectroscopic mechanism 14 and periodically modulated by the modulation mechanism 16 to become an excitation light Le suitable for carrying out the measurement.

The dichroic mirror 17 is positioned between the measurement system 20 and the sample holding section 40, allowing the measurement light coming from the measurement system 20 to directly pass through as described below, while subjecting the excitation light Le coming from the excitation light source 12 to a 90° reflection to guiding the excitation light Le toward the sample holding section 40 coaxially with the measurement light. The condensing lens 18 focuses the excitation light Le reflected by the dichroic mirror 17 onto a specific region, thereby irradiating the sample contained in the sample holding section 40. The sample absorbs the excitation light to generate heat, thus changing the refractive index of the sample by the variation in the temperature thereof.

The measurement system 20 irradiates the sample with the measurement light L2 for measuring the refractive index of the sample and measures the refractive index through the phase change in the measurement light. In the embodiment, the measurement system 20 is provided with a measurement light source 22, the required optical system, a photodetector 36, and a signal processing apparatus 38.

The measurement light source 22 comprises, for example, an He—Ne laser with an output of 1 mW. As shown in FIG. 1, the measurement light is emitted from the measurement light source 22 through a λ/2 wave plate 23 to adjust a plane of polarization of the measurement light, and thereafter split by a polarization beam splitter 24 into two mutually perpendicular polarized beams, i.e., a reference light L1 and a measurement light L2.

The reference light L1 is subjected to a shift in its frequency (frequency conversion) by the acousto-optic modulator 25A and is thereafter reflected by a mirror 26A to be input into a polarization beam splitter 28. The measurement light L2 is subjected to a shift in its frequency (frequency conversion) by the acousto-optic modulator 25B and is thereafter reflected by a mirror 26B to be input into the polarization beam splitter 28, where the measurement light L2 is combined with the reference light.

The reference light L1 passes directly through a polarization beam splitter 30 and is reflected 180° by a mirror 34 to be thereby returned to the polarization beam splitter 30. Between the polarization beam splitter 30 and the mirror 34 is interposed a ¼ wave plate 33, which rotates the plane of polarization of the reference light L1 traversing the ¼ wave plate 33 in both directions by 90°. Therefore, the reference light L1 that has been returned to the polarization beam splitter 30 is reflected 90° toward the side opposite the sample holding section 40. This reference light L1 is input to a photodetector 36 through a polarizing plate 35.

The measurement light L2, on the other hand, is reflected by 90° at the polarization beam splitter 30 toward the side of the sample holding section 40 and is led to the sample holding section 40 by passage through the ¼ wave plate 32, the dichroic mirror 17, and the condensing lens 18. The measurement light L2 is introduced into the sample as described below and is further reflected by 180° to be returned to the polarization beam splitter 30 through the ¼ wave plate 32. This measurement light L2, whose plane of polarization has been rotated 90° due to the back-and-forth traverse of the ¼ wave plate 32, passes through the polarization beam splitter 30 this time to be combined with the reference light L1 and directed to the polarizing plate 35 and the photodetector 36.

The reference light L1 and the measurement light L2 interfere with each other at the polarizing plate 35, and the intensity of the interference light is converted into an electrical signal (the measurement signal) by the photodetector 36.

The signal processing apparatus 38 samples the measurement signal at intervals of a specified sampling period and computes the phase change in the measurement light L2 (measurement light) based on the measurement signal. The signal processing apparatus 38 also generates data on the temporal variation in the phase change and, as described below, automatically assesses, based on this data, whether or not interaction is present in the sample S.

The aforementioned interference light intensity S1 is given by the following formula (1).

$$S1 = C1 + C2 \cdot \cos(2\pi \cdot fb \cdot t + \phi) \tag{1}$$

In this formula, C1 and C2 are constants determined by the optical system such as the polarization beam splitters, and by the transmittance of the sample S; $\phi$ is a phase difference due to the optical path length difference between the reference light L1 and the measurement light L2; and fb is a frequency difference between the reference light L1 and the measurement light L2. This formula (1) shows that the change in the aforementioned phase difference $\phi$ can be obtained from the change in the interference light intensity S1 (the difference between the intensity when there is no irradiation of excitation light or its intensity is weak and that when its intensity is strong). The signal processing apparatus 38 calculates the change in the phase difference φ based on formula (1).

When the intensity of the excitation light Le is periodically modulated at a frequency f, for example, by the rotation of a chopper, the refractive index of the sample S also varies with the frequency f; the optical path length of the measurement light L2 also varies with the frequency f (the optical path length of the reference light L1 is constant); and the phase difference φ also varies with the frequency f. Hence, the measurement (the calculation) of the variation in the phase difference φ for a component of the frequency f (a component with the same period as the intensity modulation period of the excitation signal) makes it possible to measure only the refractive index variation of the sample S while eliminating the influence of noise lacking a component of the frequency f. This measurement improves the S/N ratio of the measurement of the phase difference φ.

When a laser diode or LED is used as the excitation light source 12, the aforementioned modulation can be made by controlling the power source for the excitation light source 12 using electrical circuitry.

Figure 2:
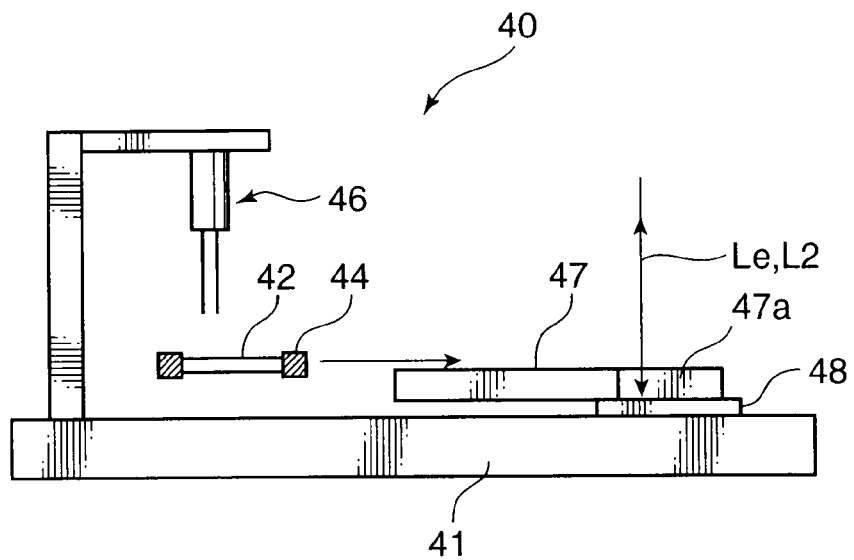
FIG. 2 is a partial cross section in front view of the sample holding section in the aforementioned detection apparatus.

The sample holding section 40 is, as shown in FIG. 2, provided with a base 41, a microarray 42 as a sample receiver, and a manipulator 44 as a transfer means. On the base 41 are disposed an automatic dispenser 46, a heater 47, and a mirror 48.

Figure 3:
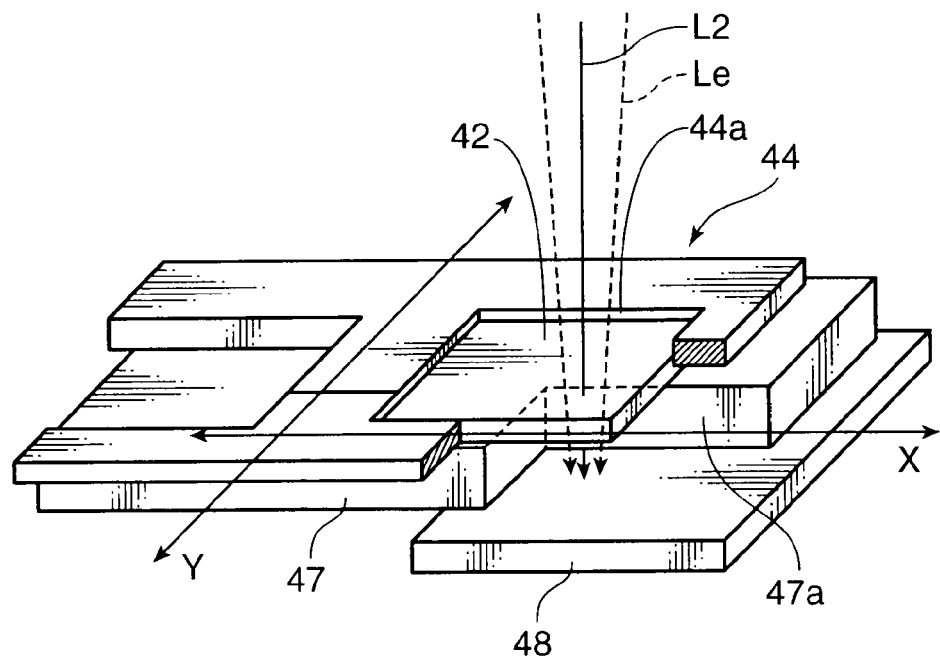
FIG. 3 is a partial cross section in perspective view that shows the relevant elements of the aforementioned sample holding section.
Figure 4A:
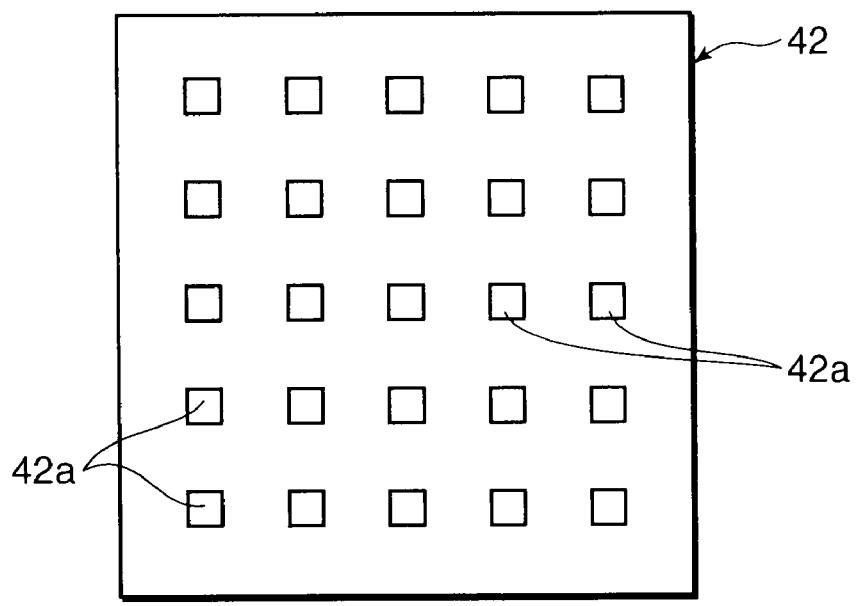
FIG. 4A is a plan view of the microarray used in the aforementioned sample holding section and FIG. 4B is a cross-sectional view of its relevant elements.
Figure 4B:
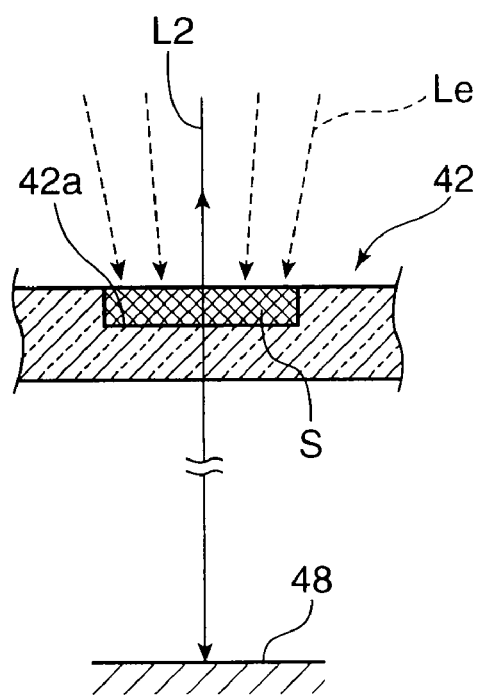

The microarray 42, which receives the sample dispensed from the automatic dispenser 46, is formed of a flat substrate as shown in FIGS. 2 to 4. In the upper surface of this microarray 42, there are formed a plurality of sample receiving concavities 42a in vertical and horizontal rows (5×5=25 concavities in the example shown in FIG. 4A), and the sample S is dispensed into each sample receiving concavity 42a as shown in FIG. 4(b). While the present invention is not limited to the specific material of the sample receiver, the material of the microarray 42 according to this embodiment is required to be transparent for the excitation light Le and the measurement light L2. Suitable specific examples are synthetic quartz, quartz, PDMS, and so forth.

The manipulator 44, having a window 44a of the shape corresponding to the outline of the microarray 42, holds the microarray 42 within the window 44a. In other words, the manipulator 44 surrounds the microarray 42 to hold it while opening the top surface and the lower surface of the microarray 42.

The automatic dispenser 46 is vertically set up above the base 41 and drops a moderate amount (i.e., an amount for filling up each individual sample receiving concavity 42a) of the sample S.

The mirror 48 is disposed on the base 41 horizontally separating from the automatic dispenser 46 to reflect upward the measurement light L2 introduced downward from the measurement system 20 by 180°.

The heater 47, which constitutes the temperature regulating mechanism according to the present invention, is provided directly above the mirror 48 to heat the microarray 42 transferred onto the heater 47 to a prescribed temperature. This heating temperature is set at a temperature that promotes the interaction between the small biomolecule and its aptamer in the sample S (that is, the reaction temperature). The heater 47 is formed with a cut-out region 47a at the location into which the excitation light Le and the measurement light L2 is irradiated, the cut-out region 47a opening the mirror 48 upward.

The temperature regulating mechanism according to the present invention is not limited to the abovementioned heater 47, but may include a cooler for lower the sample temperature.

The manipulator 44 transports the microarray 42, in the following order: the dispensing position for dispensing by the automatic dispenser 46, a heating position above the heater 47, and an irradiation position in the mirror 48 to is irradiated with the excitation light Le and the measurement light L2.

The action of this detection apparatus is described below.

In the sample holding section 40, the manipulator 44 holding the microarray 42 first transfers the microarray 42 to the dispensing position and scans the microarray 42 so as to position each of the sample receiving concavities 42a of the microarray 42 directly beneath the automatic dispenser 46. At the dispensing position, the automatic dispenser 46 dispenses the sample S into each sample receiving concavity 42a.

Following the finish of dispensing the sample S into all of the sample receiving concavities 42a, the manipulator 44 transfers the microarray 42 to the heating position over the heater 47. This heating position may be such a position that the microarray 42 comes in direct contact with the heater or may be such a position that the microarray 42 is slightly separated from the heater 47. Holding the microarray 42 in this heating position for a prescribed time can promote the reaction (interaction between the small biomolecule and its aptamer) in the sample S within each sample receiving concavity 42a.

The manipulator 44 then transfers the microarray 42 into the irradiation position, as shown in FIG. 4B, for irradiation with the excitation light Le and the measurement light L2; the irradiation position is a position directly above the mirror 48, corresponding to the cut-out region 47a of the heater 47. The manipulator 44 then scans the microarray 42 so as to let the sample S within each of the sample receiving concavities 42a in the microarray 42 be irradiated with the excitation light Le and the measurement light L2.

At this irradiation position, the excitation light Le led from the excitation system 10 to the sample holding section 40 is introduced the sample S to pass through it. At this time, the sample S absorbs the excitation light Le to thereby generate heat (the photothermal effect). On the other hand, the measurement light L2 led from the measurement system 20 to the sample holding section 40, is introduced into each sample receiving concavity 42a coaxially with the excitation light Le to pass through the sample S within the concavity 42a. This measurement light L2 is also reflected upward by the mirror 48 to re-traverse the sample S. At this time, the refractive index in the sample S varies with the amount of heat generated by the photothermal effect, which varies the phase difference φ; this means that the intensity of the interference light produced by interference between the measurement light L2 returned to the measurement system 20 and the reference light L1 in the measurement system 20 varies with the amount of heat generated. The photodetector 36 in the measurement system 20 produces a measurement signal corresponding to the interference light intensity to input it to the signal processing apparatus 38.

Figure 5:
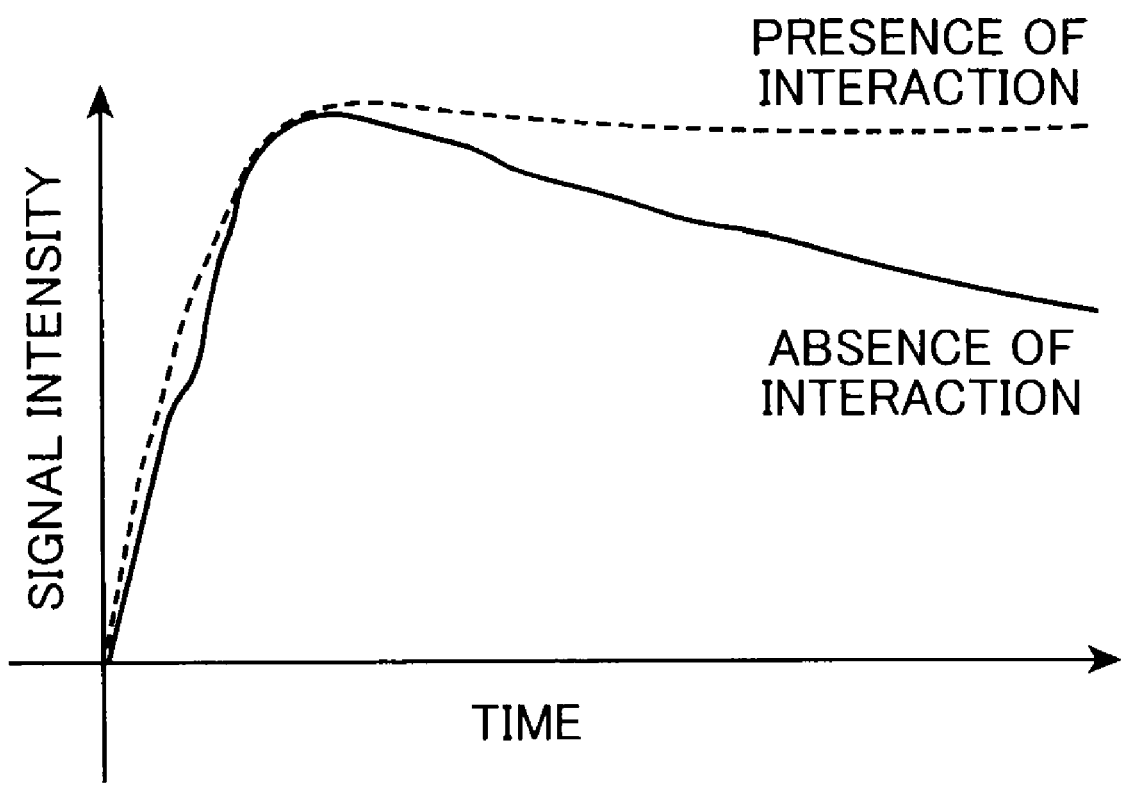
FIG. 5 is a graph of the temporal variation in the intensity of the measurement signal produced by the aforementioned detection apparatus.

The signal processing apparatus 38 acquires the measurement signal at intervals of a prescribed sampling period to generate data showing the temporal variation in the measurement signal, for example, a graph showing the relationship between elapsed time and signal intensity as shown in FIG. 5. When the small biomolecule is not present in the sample S, that is, when the interaction between the small biomolecule and its aptamer has not been produced, the signal intensity declines with elapsed time; in contrast, when the interaction has been produced, the signal intensity is maintained an almost constant value regardless of elapsed time. In view of this, the signal processing apparatus 38 determines the temporal attenuation rate in this signal intensity and makes the assessment that the interaction is present when this temporal attenuation rate is less than or equal to a prescribed value. Thus realized is the detection of the presence or absence of the small biomolecule in the sample S.

Though the temporal attenuation rate can be assessed by the operator based on the aforementioned graph, the signal processing apparatus 38, in the embodiment, automatically calculates the temporal attenuation rate to assess the presence/absence of the interaction. As a specific example that can be considered, the signal processing apparatus 38 calculates a linear approximation equation showing the temporal variation in signal intensity, based on the signal intensity acquired at intervals of the sampling period, and assess the aforementioned interaction to have been produced based on the gradient of the straight line less than or equal to a prescribed value. If the dispersion in the individual sampled signal values from the linear approximation equation is excessively large, the measurement may be assessed defective.

These method and apparatus allow the presence or absence of the interaction between a small biomolecule and its aptamer in the sample S to be detected without labeling the small biomolecule that is the detection target in the sample S or the aptamer targeted to the small biomolecule, thereby enabling low molecular weight small biomolecules to be detected with a high sensitivity.

A second embodiment is described in the following with reference to FIGS. 6 and 7. The structure of the apparatus as a whole is the same as in FIG. 1, not described again here.

Figure 6A:
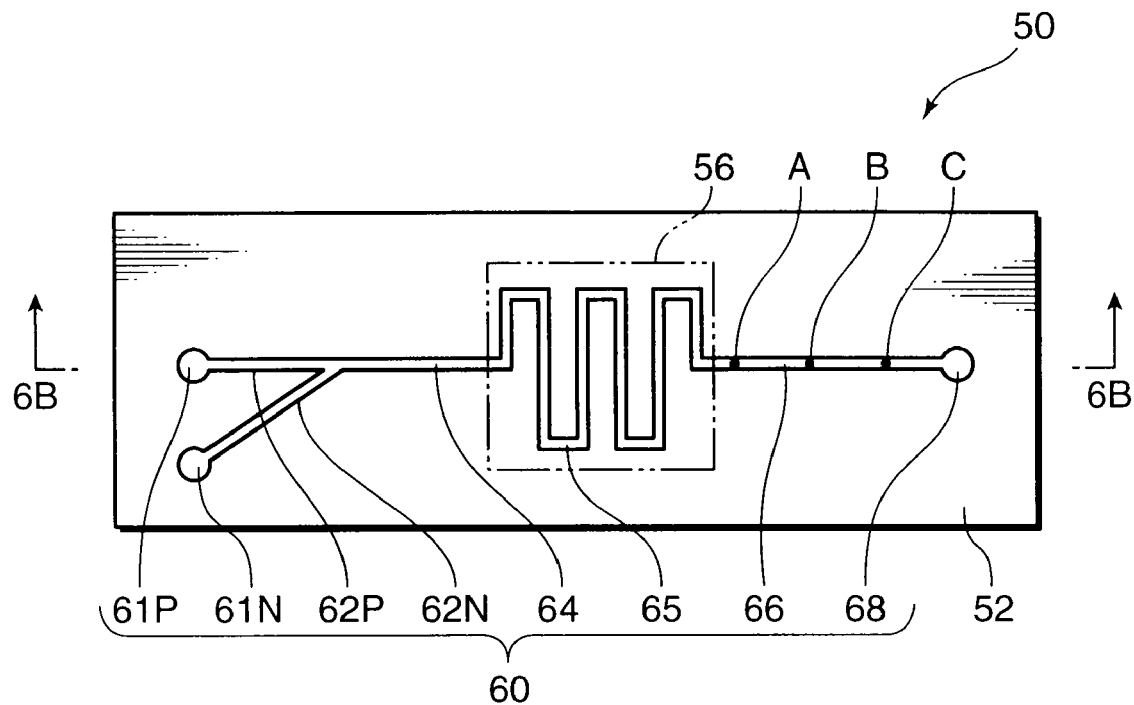
FIG. 6A is a plan view of the microreactor used in a second embodiment of the present invention and FIG. 6B is a cross-section view at the 6B-6B line in FIG. 6A.
Figure 6B:
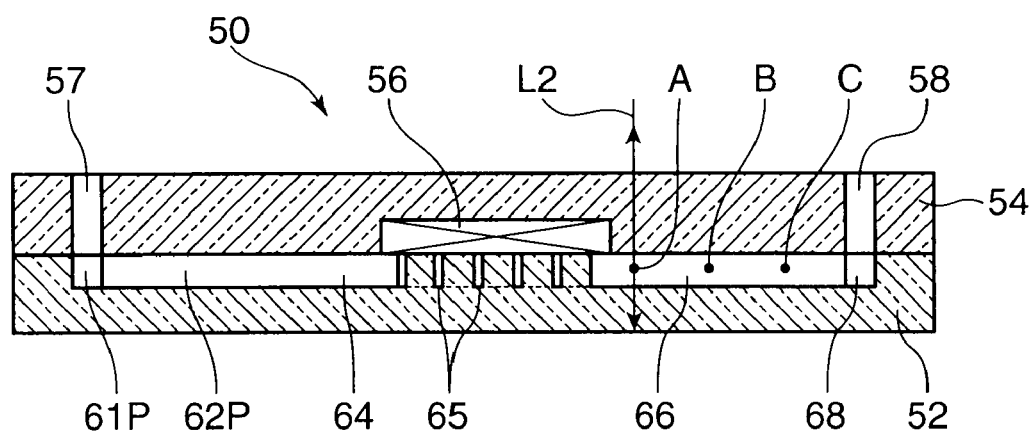

This second embodiment employs a microreactor 50 having a flow path 60 for moving the sample in a prescribed direction as shown in FIG. 6, in place of the means for transferring the microarray 42 that is the sample receiver according to the first embodiment. This microreactor 50 thus assumes both the role of the sample receiver and the role of the means for guiding the sample in the transfer direction.

This microreactor 50 comprises a lower substrate 52 and an upper substrate 54 overlaid thereon. These substrates 52, 54 are, like the microarray 42, formed of material transparent for the excitation light Le and the measurement light L2.

The flow path 60 is constituted by a groove formed in the upper surface of the lower substrate 52. The upper substrate 54 is mounted and joined onto the lower substrate 52 to seal the flow path 60.

This flow path 60 has, in order from its upstream side, a first feed section 61N and a second feed section 61P, feed flow paths 62N and 62P located downstream of the respective feed sections 61N and 61P, a common flow path 64 into which the feed flow paths 62N and 62P are joined, a reaction section 65 for reacting the small biomolecule as the detection target with the aptamer therefor, a light irradiation section 66 irradiated with the excitation light Le and the measurement light L2 along the thickness direction of the substrate, and a sample discharge section 68.

The first feed section 61N is a portion that is supplied with a first liquid possibly containing the small biomolecule to be detected (i.e., a liquid which is subject of detection), while the second feed section 61P is supplied with a liquid containing aptamer capable of interacting with the small biomolecule. The first liquid and the second liquid are flowed into the common flow path 64 to produced a sample.

The upper substrate 54 is formed with a supply port 57 for each of the feed sections 61N and 61P, each the supply port 57 penetrating through the upper substrate 54 in a thickness direction thereof. Similarly is formed a discharge port 58 for the sample discharge section 68 in the upper substrate 54. The supply ports 57 are connected to a small biomolecule input syringe and an aptamer input syringe as the sample transfer means, respectively. These syringes feed the first liquid and the second liquid through the supply ports 57 to the first feed section 61N and the second feed section 61P, respectively.

There is incorporated a heater 56 in the upper substrate 54 at a position above the reaction section 65. This heater 56 heats the sample to the small biomolecule/aptamer reaction temperature (the temperature for interaction). In order to secure a satisfactory heating time, namely, a satisfactory reaction time (for example, 10 minutes), the reaction section 65 is meandering to extend its flow path length.

The light irradiation section 66 is shaped as a straight line, in which a plurality of irradiation positions (three positions A, B, and C in the example in the drawing) for the excitation light Le and measurement light L2 are set along a lengthwise direction of the light irradiation section (that is, the sample flow direction). Either the light irradiation position for the lights Le and L2 or the microreactor 50 is so moved as to irradiate the irradiation positions sequentially with the excitation light Le and measurement light L2.

The lower substrate 52 has a bottom surface, which is coated with a reflective film (for example, a dielectric multilayer film) to provide a 180° reflection of the measurement light L2, the reflection making the measurement light L2 go and back through the sample S.

The dimensions of the flow path 60 can be established as appropriate; generally suitable are a width of about 200 μm and a depth of about 100 μm. The sample is preferably transported at a relatively low velocity, for example, about 0.5 mm/sec is suitable.

This microreactor 50 allows sample production, interaction, and measurement of the photothermal effect to be all carried out within the microreactor 50, which realizes an efficient detection of small biomolecules with a compact structure.

Figure 7A:
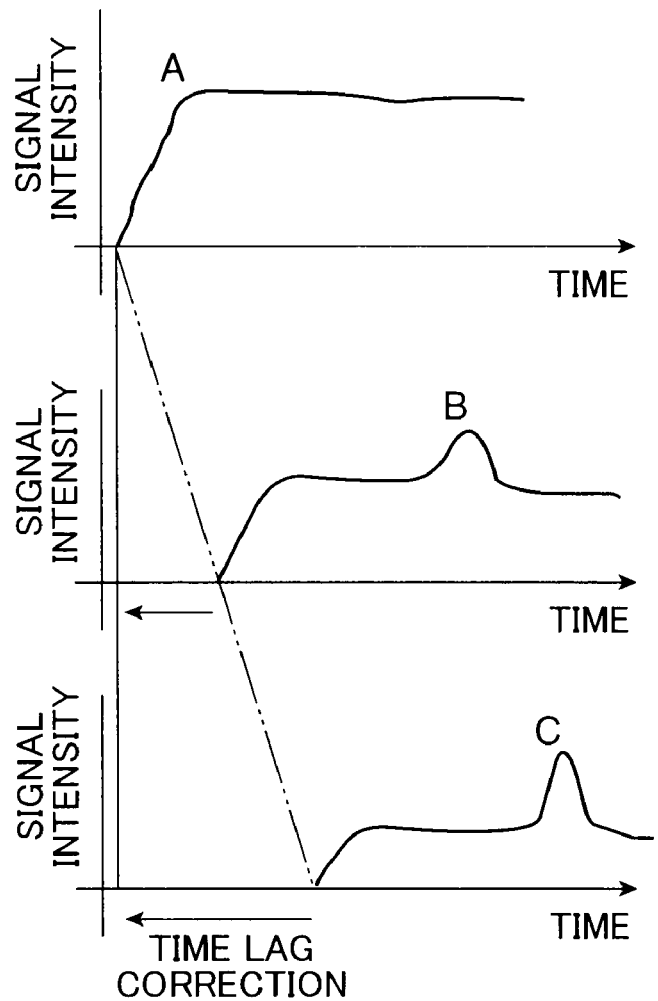
FIG. 7A is a graph that shows the temporal variation in the measurement signal obtained in the second embodiment of the present invention at each of the measurement positions A to C and FIG. 7B is a graph that shows the temporal variation in the signal yielded by superimposing these measurement signals.

In this second embodiment, signal processing is carried out, for example, as follows. When the small biomolecule, the subject of the detection, is not present in the sample, in other words, when the interaction between the small biomolecule and its aptamer has not been produced in the sample, the photothermal effect induced by irradiation with the excitation light Le attenuates with elapsed time; therefore, the detection signal intensity at a position B downstream of a position A which is the measurement start position is lower than that at the position A, and further, the detection signal intensity at a position C downstream of the position B is lower than that of the position B. On contrast, when the sample contains a section where the interaction has been produced, almost no attenuation of the photothermal effect occurs in the section; therefore, the signal strength increases transiently when the section passes position B and position C. Specifically, the signal intensity temporally varies, for example, as shown in FIG. 7A.

Figure 7B:
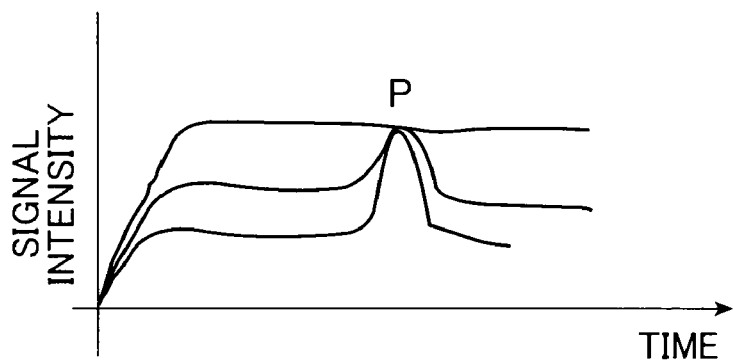

When a correction is made for the time lag among the detection signal at positions A to C and the detection signals at positions A to C are then superimposed as shown in FIG. 7B, the signal intensity is substantially increased only at the region where the aforementioned interaction has been produced (P in FIG. 7B). This makes it possible to acquire the fact that the interaction has been produced in a region having a locally high signal intensity, thereby enabling the presence of the small biomolecule in the sample to be recognized.

The signal processing apparatus 38 outputs the superimposed data as shown in FIG. 7B and further automatically assesses, based on the size of the peak value in this superimposed data, whether or not the interaction is present and whether or not the small biomolecule is present. Also in this second embodiment, like in the first embodiment described above, the irradiation position irradiated with the excitation light Le and the measurement light L2 may be disposed only at a single position, where the temporal variation is monitored; or the irradiation position irradiated with the excitation light Le and the measurement light L2 may track along at the same velocity as the flow velocity of the sample in the light irradiation section 66.

In the present invention, the method of measuring the photothermal effect induced in the sample by the excitation light is not limited to the optical interference method described in the preceding. For example, also usable is a method comprising measuring the change in the intensity of the measurement light accompanying the change in the refractive index of the solvent, such as the thermal lens method.

EXAMPLE 1

There will be demonstrated small biomolecule detection by the apparatus shown in FIGS. 1 to 4.

A synthetic quartz microarray is used for the microarray 42 shown in FIGS. 4A and 4B, the sample receiving concavities 42a therein having the shape of a 0.5 mm×0.5 mm×1.0 mm rectangular parallelepiped (this shape, however, may also be that of a cylindrical column with a diameter of 0.5 mm).

Dispensed into each of the sample receiving concavities 42a is a solution containing an aptamer (a functional polymer comprising nucleic acid) that specifically reacts with adenosine (a small biomolecule), which is heated with the heater 47 to 75° C. and held at the temperature for 15 minutes. The temperature is subsequently maintained at 25° C. by the heater 47 for 15 minutes. Thereafter, for preparing an adenosine-containing sample, they are so mixed as to provide a final adenosine aptamer concentration of 1.3 μM and a final adenosine concentration of 7.4 μM. This mixing is not performed in the preparation of the sample lacking adenosine.

The sample is then held at 25° C. by the heater 47, and this condition is maintained for the time (5 minutes) required for the reaction (interaction). The sample is thereafter set in the irradiation position for irradiation thereafter set in the irradiation position for irradiation with the excitation light Le and measurement light L2 and measurement of the photothermal effect in the sample is carried out. Used for the light source 12 for the excitation light Le is a high-pressure mercury lamp, in which the region of the emission maximum around the wavelength of 250 nm is extracted by a band pass filter to be modulated to about 80 Hz with an optical chopper; the light is focused to a region with a diameter of 5 mm and directed onto the sample. The sample is irradiated also with the measurement light L2 coaxially with this excitation light Le and the intensity of the interference light from this measurement light L2 and the reference light L1 is measured. This measurement signal is displayed as a voltage value at the signal processing apparatus 38 and continuously recorded by a data logger.

Figure 8:
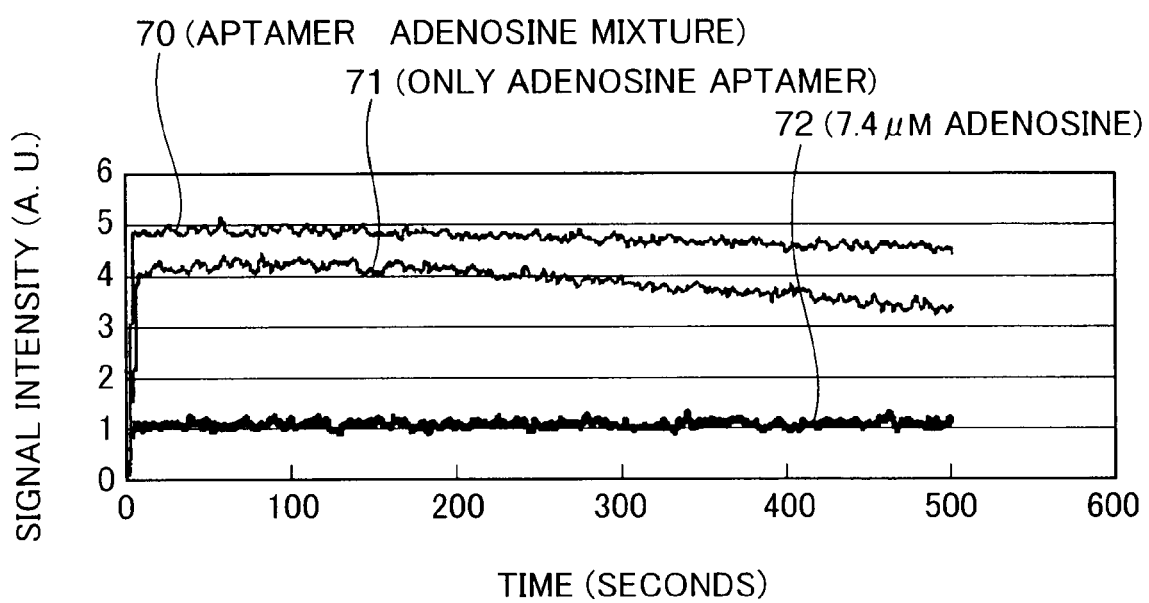
FIG. 8 is a graph that shows the measurement signal obtained by the operation of the apparatus according to the first embodiment.

The results of this measurement are shown in FIG. 8. As shown by the line 71 in FIG. 8, in the case of the sample containing only aptamer, the intensity of the measurement signal rises and thereafter gradually declines with elapsed time. In the case of the sample containing only adenosine, the signal intensity does not even rise, as shown by the line in FIG. 8. On contrary, in the case of the sample containing both adenosine and its aptamer, the signal intensity rises and thereafter almost no decline in the signal intensity is seen, as shown by the line 70 in FIG. 8.

Accordingly, the rates of decline after the rise in signal strength enables the presence of adenosine in the sample to be assessed. Specifically, it has been confirmed that the presence of adenosine mixed with aptamer can be detected to about 40 nM.

As has been described in the preceding, the detection method and apparatus according to the present invention allows a small biomolecule in the sample to be reliably detected by use of simple and inexpensive instrumentation, based on the temporal variation in the photothermal effect in a sample induced by irradiating the sample with an excitation light. This detection method specifically comprises a step of irradiating a sample containing aptamer capable of interacting with the small biomolecule with an excitation light; a step of measuring a photothermal effect produced in the sample by the irradiation with the excitation light; and a step of assessing whether or not an interaction between the small biomolecule and its aptamer has been produced based on the temporal variation in this photothermal effect to detect the presence or absence of the small biomolecule. The detection apparatus is one for detecting a small biomolecule in a sample, comprising a sample holding section for holding a sample containing an aptamer that can interact with the small biomolecule; an excitation light irradiation system that irradiates the sample held in the sample holding section with an excitation light; and a measurement apparatus that produces a measurement signal for a photothermal effect produced in the sample by the irradiation with the excitation light, the measurement apparatus having a signal processing apparatus that generates data on the temporal variation in the measurement signal and assesses, based on the generated data, whether or not the interaction is present to detect the presence or absence of the small biomolecule.

The photothermal effect measurement step in the detection method preferably comprises making a measurement light other than the excitation light pass through the sample and measuring a phase change of the passed-through measurement light. Similarly, the measurement apparatus in the detection apparatus preferably makes a measurement light other than the excitation light pass through the sample and measures the phase change of the passed-through measurement light. Since heat generation caused in the sample by photothermal effect changes the refractive index of light at the sample, making a measurement light pass through the sample and measuring the phase change in the measurement light enables the photothermal effect in the sample to be facilely and accurately evaluated.

In this case, the measurement apparatus preferably comprises a measurement light source; an optical system making the measurement light emitted from the measurement light source pass through the sample held in the sample holding section to cause the passed-through measurement light to interfere with a reference light; and a photodetector that detects the intensity of the interference light.

This measurement apparatus can easily measure the phase change of the measurement light passing through the sample by use of a simple structure for merely detecting the intensity of the interference light given by the interference between the measurement light and reference light.

The sample holding section preferably comprises a sample receiver that receives the sample; a temperature regulating mechanism that regulates the sample in the sample receiver to a reaction temperature for the reaction of the small biomolecule and its aptamer; and transfer means for transferring the heated sample to a position for irradiation with the excitation light.

This structure makes it possible to carry out the reaction (interaction) between the small biomolecule and its aptamer in the sample resident in the sample receiver and then directly irradiate the sample in the sample receiver with the excitation light.

The transfer means preferably transfers the sample receiver in the following sequence; to an injection position where the sample is injected into the sample receiver; a temperature regulation position where the temperature of the injected sample is regulated by the temperature regulating mechanism; and the position for irradiation with the excitation light.

The sample receiver may have a flow path for flowing the sample therethrough, the flow path having, in sequence from the upstream side, a first introduction section and a second introduction section for introducing a first liquid to be subjected to detection of the small biomolecule and a second liquid containing an aptamer for the small biomolecule respectively, a mixing section for combining and mixing the introduced first liquid and second liquid, a reaction section for regulating the temperature of the resulting mixed liquid with the temperature regulating mechanism to cause the reaction between the small biomolecule and the aptamer, and an excitation light irradiation section which is irradiated with the excitation light. This sample receiver enables small biomolecule detection to be carried out very efficiently using a compact structure.

When the excitation light irradiation section is irradiated with the excitation light at a plurality of positions disposed along the sample flow direction, measuring the photothermal effect at each position allows the temporal variation of the photothermal effect to be correctly detected.

The invention claimed is:

1. A method of detecting a small biomolecule in a sample, comprising:
   a step of irradiating a sample containing an aptamer that can interact with the small biomolecule with an excitation light;
   a step of measuring a photothermal effect produced in the sample by the irradiation with the excitation light; and
   a step of assessing, on the basis of the temporal variation in the photothermal effect, whether or not interaction between the small biomolecule and aptamer has occurred in the sample to detect the presence or absence of the small biomolecule.

2. The method of detecting a small biomolecule according to claim 1, wherein the step of measuring a photothermal effect comprises making a measurement light other than the excitation light pass through the sample and measuring the phase change of the passed-through measurement light.

3. An apparatus for detecting a small biomolecule in a sample, comprising:
   a sample holding section for holding a sample containing an aptamer that can interact with the small biomolecule;
   an excitation light irradiation system that irradiates the sample held in the sample holding section with an excitation light; and
   a measurement apparatus that produces a measurement signal for a photothermal effect produced in the sample by the irradiation with the excitation light,
   wherein the measurement apparatus comprises a signal processing apparatus that generates data on the temporal variation in the measurement signal and assesses, based on the generated data, whether or not interaction between the small biomolecule and the aptamer has occurred in the sample to detect the presence or absence of the small biomolecule by.

4. The apparatus for detecting a small biomolecule according to claim 3, wherein the measurement apparatus makes a measurement light other than the excitation light pass through the sample and measures the phase change of the passed-through measurement light.

5. The apparatus for detecting a small biomolecule according to claim 4, wherein the measurement apparatus comprises:
   a measurement light source;
   an optical system that makes the measurement light emitted from the measurement light source pass through the sample held in the sample holding section and causes the passed-through measurement light to interfere with a reference light; and
   a photodetector that detects the intensity of the interference light.

6. The apparatus for detecting a small biomolecule according to claim 3, wherein the sample holding section comprises:
   a sample receiver that receives the sample;
   a temperature regulating mechanism that regulates the sample in the sample receiver to a reaction temperature for the reaction of the small biomolecule and its aptamer; and
   a transferrer for transferring the heated sample to a position for irradiation with the excitation light.

7. The apparatus for detecting a small biomolecule according to claim 6, wherein the transferrer transfers the sample receiver, in the following sequence, to an injection position where the sample is injected into the sample receiver, a temperature regulation position where the temperature of the injected sample is regulated by the temperature regulating mechanism, and the position for irradiation with the excitation light.

8. The apparatus for detecting a small biomolecule according to claim 6, wherein the sample receiver has a flow path for flowing the sample therethrough, the flow path having, in sequence from the upstream side, a first introduction section and a second introduction section for introducing a first liquid to be subject to detection of the small biomolecule and a second liquid containing an aptamer for the small biomolecule respectively, a mixing section for combining and mixing the introduced first liquid and second liquid, a reaction section for regulating the temperature of the resulting mixed liquid with the temperature regulating mechanism and carrying out the reaction between the small biomolecule and the aptamer, and an excitation light irradiation section which is irradiated with the excitation light.

* * * * *